United States Patent [19]

Taylor et al.

[11] 4,395,421

[45] Jul. 26, 1983

[54] DISODIUM CROMOGLYCATE FORMULATIONS

[75] Inventors: James E. Taylor, Loughborough; Neil A. Stevenson, Nanpantan, both of England

[73] Assignee: Fisons Limited, Ipswich, England

[21] Appl. No.: 67,104

[22] Filed: Aug. 16, 1979

Related U.S. Application Data

[63] Continuation of Ser. No. 830,617, Sep. 6, 1977, abandoned.

[30] Foreign Application Priority Data

Oct. 16, 1976 [GB] United Kingdom ............... 43054/76

[51] Int. Cl.$^3$ .............................................. A61K 31/35
[52] U.S. Cl. .................................................. 424/283
[58] Field of Search ........................................ 424/283

[56] References Cited

U.S. PATENT DOCUMENTS 4,046,910 9/1977 Johnson ............................ 424/283

OTHER PUBLICATIONS

Remington's Pharmaceutical Sciences, 13th ed., pp. 568–572, (1965).

*Primary Examiner*—Leonard Schenkman
*Attorney, Agent, or Firm*—Merriam, Marshall & Bicknell

[57] ABSTRACT

There is described disodium cromoglycate in a form having a bulk density of greater than 0.45 g per ml when measured according to British Standard Test No 1460 (1967).

There are also described granular and unit dosage forms of disodium cromoglycate. The disodium cromoglycate is useful, e.g. in the treatment of certain conditions of the gastrointestinal tract.

14 Claims, No Drawings

DISODIUM CROMOGLYCATE FORMULATIONS

This is a continuation of application Ser. No. 830,617, filed Sept. 6, 1977, now abandonded.

This invention concerns a pharmaceutical formulation and a unit dosage form containing disodium cromoglycate.

The disodium salt of 1,3-bis(2-carboxychromon-5-yloxy)propan-2-ol (disodium cromoglycate or cromolyn sodium) is a known medicament useful in the treatment of asthma and of various disorders of the gastrointestinal tract in which allergic or immune reactions play a part. For treatment of these latter disorders it is often convenient to present the medicament at least initially in the form of a powder. However finely powdered sodium cromoglycate flows very poorly, and is extremely difficult to fill into capsules with any acceptable degree of accuracy of dose unless a flow aid, for example lactose, is incorporated therewith. In some conditions and with some patients, such flow aids may prove to be allergens themselves.

Furthermore with disodium cromoglycate in finely divided or soft pellet or soft granule form it has not been found possible to fill a sufficient quantity of the drug into compact and easily swallowed form, e.g. into a normal capsule. Indeed in practice only 10 or 20 mg of disodium cromoglycate (in admixture with lactose) has heretofor been loosely filled into capsules, the capsules being about one third full.

While many drugs are granulated for use as intermediates in the production of other pharmaceutical formulations, e.g. tablets, it is usual for the drugs to be granulated using binders or other excipients. Furthermore it is most unusual for granulated drugs to be filled into capsules.

Again it is known for drugs to be put up in capsules, but in so doing it is normal to include a lubricant or other pharmaceutical flow aid to enable the drug to be filled into the capsules.

We have also found that certain particle sizes of disodium cromoglycate are easier to fill into capsules than are other sizes.

According to the invention we provide disodium cromoglycate in a form having a bulk density of greater than 0.45 g per ml when measured according to British Standards Institution Test No. 1460 (1967).

We prefer the disodium cromoglycate to have a bulk density of from 0.5 to 0.7, and more preferably from 0.53 to 0.66, g per ml. We also prefer the disodium cromoglycate to be in hard granular form.

The disodium cromoglycate preferably contains less than 5%, more preferably less than 1%, by weight, and most preferably none of any other compound, with the exception of water.

Desirably the disodium cromoglycate is substantially free from (i.e. less than 20% by weight consists of) particles of greater than 250, and preferably greater than 200, microns diameter. Desirably also, not more than 60% by weight consists of particles of less than 60, more desirably less than 80, and most desirably less than 90, microns diameter. In a particular embodiment of the invention the disodium cromoglycate is substantially free of (i.e. less than 20% by weight consists of) particles of less than 60, and preferably less than 45, microns diameter.

We particularly prefer the disodium cromoglycate to be substantially free of particles outside the range of 60 to 200 microns diameter. Particle sizes referred to herein are as measured by sieve analysis unless otherwise stated.

The disodium cromoglycate granules may be prepared by micronising disodium cromoglycate to a particle size substantially (i.e. greater than 90% by weight) less than 10 microns (as measured by a Coulter counter) (although this step may be omitted if desired) adding water and mixing to give a moisture content of from 15 to 35% by weight (more preferably from 20 to 30%, most preferably 21 to 26%, and especially 22 to 24%, by weight), passing the admixture through a granulator fitted with a screen of mesh size 4 to 30 apertures per inch, drying to a moisture content of from 5 to 8% by weight, and sieving to obtain granules of the required range of diameters.

The higher the rate at which the water is added, the higher, generally speaking, is the proportion of coarse particles (i.e. above 250 microns). It is therefore preferred that the rate of addition of the water be less than 2% by weight per minute based on the total original weight of the disodium cromoglycate, including any water originally present. The rate is more preferably from 0.5 to 1.5% by weight per minute. The water addition is preferably effected so as to mix the water with the disodium cromoglycate as intimately as possibe. It is thus preferred to add the water by spraying, and to stir or agitate during mixing.

The granulator employed is preferably an oscillating granular fitted with a 20 or 24 mesh screen. The granulation temperature can also affect particle size distribution, giving rise to high proportions of coarse particles at higher temperatures. The granulation bed temperature is thus preferably less than 50° C. and more preferably from 40° to 50° C.

Drying is preferably effected in a preheated forced convection hot air oven or a fluidised bed dryer. The temperature for drying is desirably from 60° to 100° C., and more especially from 75° to 85° C.

Sieving to remove the particles of diameter greater than the desired largest size and lower than the desired lowest size is preferably achieved by passing the dried particles through one or more appropriate screens.

According to the invention we also provide a unit dosage form containing from 1 to 250 mg of disodium cromoglycate, at least part of the DSCG being in granular form.

The unit dosage forms according to the invention preferably comprise granules enclosed in a suitable membrane, e.g. in a sachet such as a rice paper sachet, or preferably a capsule e.g. a gelatin capsule. We prefer the unit dosage forms, and in particular the granules in the unit dosage forms, not to contain a lubricant.

When a capsule is used we prefer the capsule to contain no colouring matter.

Thus according to a further feature of our invention we provide a unit dosage containing more than 10%, and preferably more than 50%, by weight of granular disodium cromoglycate, from 5 to 12% by weight of water, and from 35 to 85% by weight of encapsulating material, e.g. gelatin.

When the unit doses according to the invention are capsules the capsules are preferably from 10 to 100, more preferably from 20 to 80, and most preferably from 60 to 80%, full when loosely filled.

The unit dosage forms and the granules according to the invention are useful in the treatment of conditions of the gastrointestinal tract in which conditions allergic reactions play a contributory part, e.g. milk allergy. For these uses a dosage of from about 5 to 250 mg of disodium cromoglycate may be used. The unit dosage forms and the granules according to the invention are also useful for the treatment of allergic conditions of the nose, e.g. hay fever, and for such conditions a dosage of from about 1 to 10 mg of disodium cromoglycate may be used.

Capsules according to the present invention may, by reason of the greater density of the granules, contain up to three times the weight of conventional micronised disodium cromoglycate or up to twice the weight of disodium cromoglycate in soft pellet form which can be filled into a particular size of capsule.

The invention will now be further described, though only by way of illustration, in the following Examples.

EXAMPLE 1

2000 g of micronised disodium cromoglycate of determined water content was placed in the bowl of a planetary mixer. The calculated amount of water (approximately 500 g) to bring the moisture content of the disodium cromoglycate to within the range 22 to 24% by weight was then added by spraying, the sides of the mixer bowl being scraped regularly to ensure even moisture distribution. The damp disodium cromoglycate was passed through an oscillating granulator fitted with a 8 mesh screen and then through a 24 mesh screen. The product was then dried in a preheated forced convection hot air oven at 80° C. for 3 hours until the moisture content of the granules was in the range 5 to 8% by weight. The granules were then sieved through a 250 micron screen to give a fraction free of particles of diameter greater than that size. (The sieved product may then optionally be sieved using an air jet sieve to remove particles of diameter less than 40 microns). The resulting granules were found to flow well and could be filled easily into gelatin capsules. It was found that about 250 mg of the granules could be filled into a standard clear No 0 capsule.

EXAMPLE 2

30 Kg of micronised disodium cromoglycate was analysed for its water content and, in a Hobart mixer, the necessary volume of water to bring the water content to 22% w/w was sprayed on at a rate of 300 ml/minute. The wetted powder was then passed through an 8 mesh screen, then through a 20 mesh screen on an oscillating granulator. The granules were then dried at 80° C. to a moisture content of less than 8% w/w, and were finally passed through a 60 mesh screen.

Batches of disodium cromoglycate made by this technique had a bulk density of from 0.60 to 0.68 g per ml.

We claim:

1. Disodium cromoglycate produced by wet granulation in a form having a bulk density of from 0.34 to 0.7 g per ml. and containing less than 5% by weight of any other compound, with the exception of water.

2. Disodium cromoglycate according to claim 1 having a bulk density of from 0.53 to 0.66 g per ml.

3. Disodium cromoglycate according to claim 1 in hard granular form.

4. Disodium cromoglycate according to claim 1 containing none of any other compound, with the exception of water.

5. Disodium cromoglycate according to claim 1 in particulate form, wherein less than 20% by weight of the particles are greater than 200 microns in diameter.

6. Disodium cromoglycate according to claim 1 in particulate form, wherein not more than 60% by weight consists of particles of less than 60 microns diameter.

7. Disodium cromoglycate according to claim 1, wherein less than 20% by weight consists of particles of less than 60 microns diameter.

8. A unit dosage form containing 1 to 250 mg of disodium cromoglycate produced by wet granulation in a granular form having a bulk density of from 0.45 to 0.7 g per ml. and less than 5% by weight of any other compound, with the exception of water.

9. A unit dosage form according to claim 8 and containing no lubricant.

10. A unit dosage form according to any of claims 8 or 9 comprising a capsule which is from 60 to 80% full when loosely filled.

11. A unit dosage form of disodium cromoglycate produced by wet granulation containing more than 10% by weight of granular disodium cromoglycate having a bulk density of from 0.45 to 0.70 g per ml., from 5 to 12% by weight of water, and from 35 to 85% by weight of encapsulating material.

12. A unit dosage form according to claim 11 containing more than 50% by weight of granular disodium cromoglycate.

13. A method for alleviating the symptoms of a disorder of the gastrointestinal tract in which an allergic reaction is involved which comprises oral administration of an effective amount of disodium cromoglycate according to claim 1 to a patient suffering from such a condition.

14. A method for alleviating the symptoms of a disorder of the nose in which an allergic reaction is involved which comprises intranasal administration of an effective amount of disodium cromoglycate according to claim 1 to a patient suffering from such a condition.

* * * * *